United States Patent [19]
Shoemaker

[11] Patent Number: 6,124,461
[45] Date of Patent: Sep. 26, 2000

[54] COMPOUNDS, COMPOSITIONS, AND METHODS FOR TREATING ERECTILE DYSFUNCTION

[75] Inventor: James D. Shoemaker, Clayton, Mo.

[73] Assignee: Saint Louis University, Health Services Center, Research Administration, St. Louis, Mo.

[21] Appl. No.: 09/084,849

[22] Filed: May 26, 1998

[51] Int. Cl.$^7$ ...................... C07D 217/10; C07D 233/54
[52] U.S. Cl. ........................................ 546/147; 548/334.5
[58] Field of Search .......................... 546/147; 548/334.5

[56] References Cited

U.S. PATENT DOCUMENTS

| | | | |
|---|---|---|---|
| 4,801,587 | 1/1989 | Voss et al. | 514/288 |
| 5,145,852 | 9/1992 | Virag | 514/248 |
| 5,242,391 | 9/1993 | Place et al. | 604/60 |
| 5,447,912 | 9/1995 | Gerstenberg et al. | 514/12 |
| 5,482,039 | 1/1996 | Place | 128/653.1 |
| 5,552,157 | 9/1996 | Yagi et al. | 424/450 |
| 5,565,466 | 10/1996 | Gioco et al. | 514/280 |
| 5,567,706 | 10/1996 | Gavras | 514/280 |
| 5,583,144 | 12/1996 | Kral | 514/321 |
| 5,648,350 | 7/1997 | DeLignieres et al. | 514/178 |
| 5,658,936 | 8/1997 | Kifor et al. | 514/381 |

OTHER PUBLICATIONS

Hellstrom et al. "A double–blind, placebo–controlled evaluation of the erectile response to transurethral alprostadil" *Urology* 1996;48(6):851–6.

Padma–Nathan et al. "Treatment of men with erectile dysfunction with transurethral alprostadil" Medicated Urethral System for Erection (MUSE) Study Group *N Eng J Med* 1997 Jan;336(1):1–7.

Purvis et al. "Determinants of satisfactory rigidity after intracaverosal injection with prostaglandin E1 in men with erectile failure" *Int J Impot Res* 1996;8(1):9–16.

Hedlund et al. "Pharmacotherapy in erectile dysfunction agents for self–injection programs and alternative application models" *Scand J. Urol Nephrol Suppl* 1996;179:129–38.

Schramek et al. "Intracavernous injection of prostaglandin $E_1$ plus procaine in the treatment of erectile dysfunction" *J. Urol* 1994;152:1108–1110.

Kattan, S. "Double–blind randomized crossover study comparing intracorporeal prostaglandin E1 with combination of prostaglandin E1 and lidocaine in the treatment of organic impotence" *Urology* 1995 Jun;45(6):1032–6.

Wolfson et al. "Intraurethral prostaglandin E–2 cream: a possible alternative treatment for erectile dysfunction" *Urology* 1993;42:73–5.

Schouman et al. "Suppression of prostaglandin E–1 induced pain by dilution of the drug with lidocaine before intracavernosal injection" *J. Urology* 1992;148:1226, letter.

Tanaka, T. "Papaverine hydrochloride in peripheral blood and the degree of penile erection" *J. Urology* 1990;143:1135–7.

Cawello et al. "Pharmacokinetics of prostaglandin E1 and its main metabolites after Intracavernous injection and short–term infusion of prostaglandin E1 in patients with erectile dysfunction" *J. Urol* 1997 Oct;158(4):1403–7.

Sundaram et al, "Long–term follow–up of patients receiving injection therapy for erectile dysfunction" *Urology* 1997 Jun;49(6):932–5.

Soderahl et al. "Intracavernosal drug–induced erection therapy versus external vacuum devices in the treatment of erectile dysfunction" *Br J. Urol* 1997 Jun;79(6):952–7.

McMahon, CG "Nonsurgical treatment of cavernosal venous leakage" *Urology* 1997 Jan;49(1):97–100.

Hellstrom et al. "A double–blind, placebo–controlled evaluation of the erectile response to transurethral alprostadil" *Urology* 1996 Dec;48(6):851–6.

Chen et al. "The lowest effective dose of prostaglandin E1 as treatment for erectile dysfunction" *J. Urol* 1995 Jan;153(1):80–1.

National Institutes of Health: Impotence. Consensus Development Conference Statement. *Int J. Imp Res* 1993;5:181.

McMahon, CG "A comparison of the response to the intracavernosal injection of a combination of papaverine and phentolaime, Prostaglandin E–1 and a combination of all three agents in the management of impotence" *Int. J. Impot Res* 1991;3:113.

Shenfeld et al. "Papaverine–phentolamine and prostaglandin E1 versus papaverine–phentolamine alone for intracorporeal injection therapy: a clinical double–blind study" *J. Urol* 1995 Sep;154(3):1017–9.

Lue et al. "Impotence [editorial]" *J. Urol* 1995 Jul;154(1):85.

Virag, R. "Intracavernous injection of papaverine for erectile failure" *Lancet* 1982;2:938.

Brindley, GS "Cavernosal alpha–blockage: a new technique for investigating and treating erectile impotence" *Br J. Psychiatry* 1983;143:332.

Furlow, W.L. "Prevalence of impotence in the United States" *Med. Aspects Hum Sex* 1985 19:13–8.

(List continued on next page.)

*Primary Examiner*—Zinna Northington Davis
*Attorney, Agent, or Firm*—Darby & Darby, P.C.

[57] ABSTRACT

Vasoactive compounds are described for the treatment of erectile dysfunction and impotence. The compounds are reaction products of an anionic or negatively charged vasoactive or erection-inducing component and a cationic or positively charged vasoactive or erection-inducing component. These components are combined as acids and bases to form an organic salt or ionically bonded compound. The compounds have advantageous solubility characteristics and efficacy. A compound of the invention is combined with a pharmaceutical vehicle to form a composition which preferably includes an emulsifier. A local anesthetic and/or androgenic steroids may also be included. Compositions of the invention may also include more than one vasoactive organic salt compound. The composition can be advantageously formulated and administered to allow self-adjusted dosing, while minimizing or preventing overdosing.

19 Claims, 13 Drawing Sheets

OTHER PUBLICATIONS

Flynn et al. "Long–term follow–up of patients with erectile dysfunction commenced on self injection with intracavernosal papaverine with or with phentolamine" *J. Urology* 1996 Oct; 78(4):628–631.

Lea et al. "Intracavernous Alprostadil A Review of its Pharmacodynamic and Pharmacokinetic Properties and Therapeutic Potential in Erectile Dysfunction" *Drugs & Aging* 1996 Jan;8(1):56–74.

Vaidyanathan et al. "Myocardial infarction associatd with intra–cavernosal administration of alprostadil in a patient with spinal cord injury and paraplegia" [letter] *Spinal Cord* 1996 Dec;34(12):754–5.

Chiang et al. "Papaverine and Prostaglandin $E_1$ Gel Applications for Impotence" *Ann Acad Med Singapore* 1995 Sep;24(5):767–9.

Kim et al. "Papaverine Topical Gel for Treatment of Erectile Dysfunction" *J.Urol.* Feb 1995, 153(2):361–5.

Seidmon et al. "The pH Analysis of Papaverine–Phentolamine and Prostaglandin $E_1$ for Pharmacologic Erection" *J. Urology* 1989 Jun.;141:1458–9.

Godschalk et al. "Alkalization Does Not Alleviate Penile Pain Induced By Intracavernous Injection of Prostaglandin E1" *J Urol* 1996 Sep;156(3):999–1000.

Tostain, et al. "Traitement des troubles erectiles par les androgenes: Quand? Comment?," [Androgen Treatment of Erectile Dysfunction: When? How?] Progres en Urologie, vol. 7, pp. 314–319 (1997).

Marin, "Testosterone and Regional Fat Distribution," Obesity Research, vol. 3, Suppl., pp. 609s–611s (Nov. 4 1995).

MUSE description sheet, two pages, dated Nov. 1996.

Physician Desk Reference, misc. pp. 864–865 (1997).

Physician Desk Reference misc. p. 1523 (1997).

Scala et al., "Male Erectile Dysfunction", Feb. 12, 1998.

Govier et al., "Timing of Penile Color Flow Duplex Ultrasonography Using a Triple Drug Mixture", The Journal of Urologie, vol. 153, pp. 1472–1475 (1995).

Porst, "The Rationale for Prostaglandin E1 In Erectile Failure: A survey of Worldwide Experience", The Journal of Urolgie, vol. 155, pp. 802–815 (1996).

Porst, "The Rationale For Prostaglandin E1 in Erectile Failure: a Survey of Worldwide Experience", "The Virtual Medical Center," mediconsult.com, pp. 1–3 (date unknown).

Bechara et al., "Prostaglandin E1 Versus Mixture of Prostaglandin E1, Papaverine and Phentolamine in Nonresponders To High Papaverine Plus Phentolamine Doses", The Journal of Urologie, vol. 155, pp. 913–914 (1996).

Fallon, "Intracavernous Injection Therapy For male Erectile Dysfunction", Urologic Clinics of North America, vol. 22, No. 4, pp. 833–845 (1995).

Bennett et al., 514 Abstract of: "An Improved Vasoactive Drug Combination For A Pharmacological Erection Program (PEP)", undated.

Sikora et al., 516 Abstract of: "Subjective and Objective Success–Parameters After Dorsal Venous Ligature In Erectile Dysfunction", undated.

Chao et al., excerpt from: "Experience with Intracavernosal Tri–mixture for the Management of Neurogenic Erectile Dysfunction", Medical Center Compounding Pharmacy, Intracorporeal Injections, (two pages)(undated).

"Urethra and Penis—disorders of function", Chapter 32, pp. 521–523, (unknown author) (origin unknown).

"Treating Impotence With Hormones and Drugs", pp. 143–147, (unknown author) (origins unknown).

"Injection of the Corpora Cavernosa With Pharmacologic Agents (Papaverine, Phentolamine)", pp. 1–4 (1995).

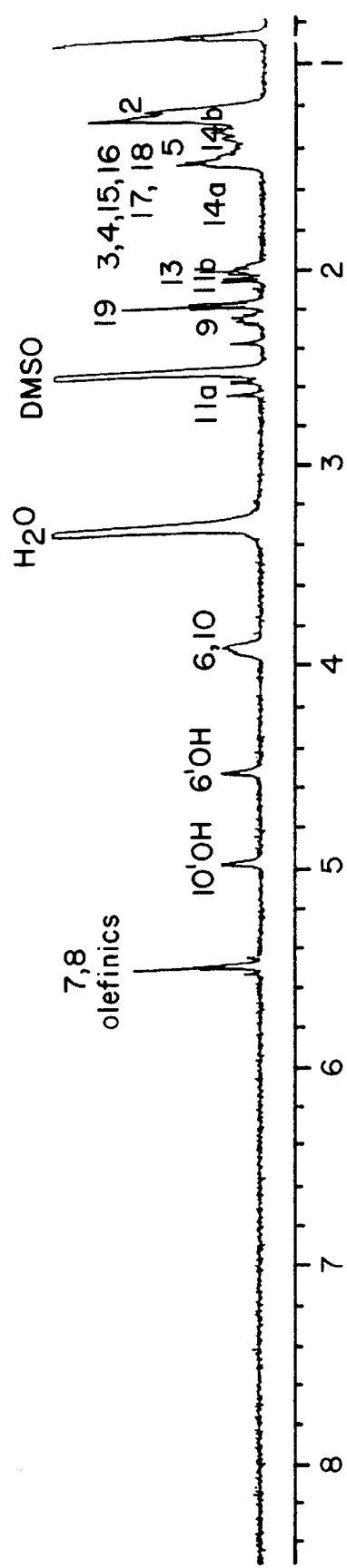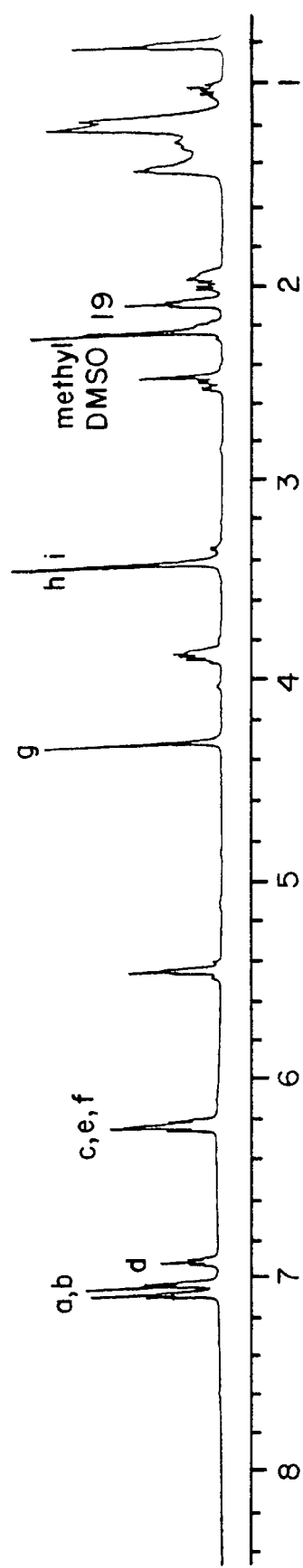

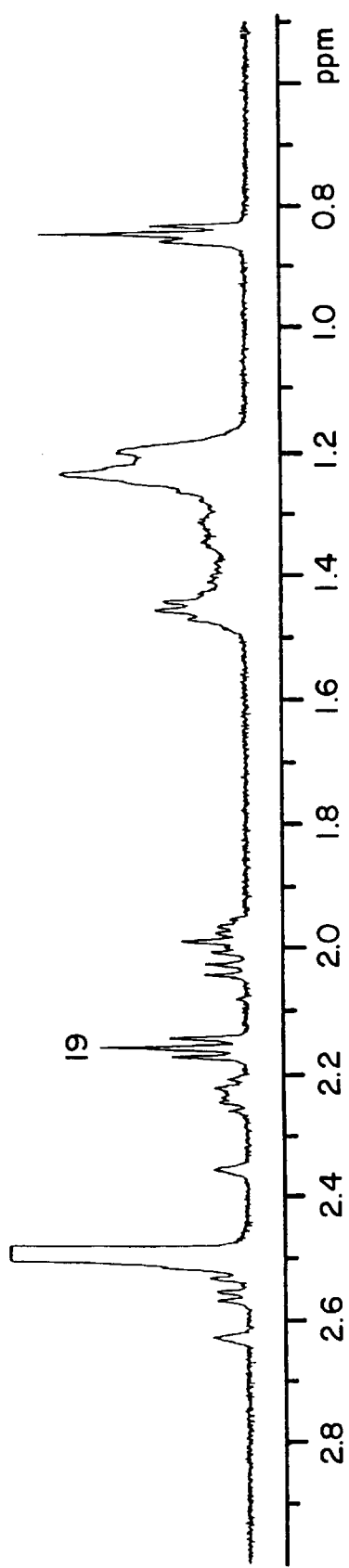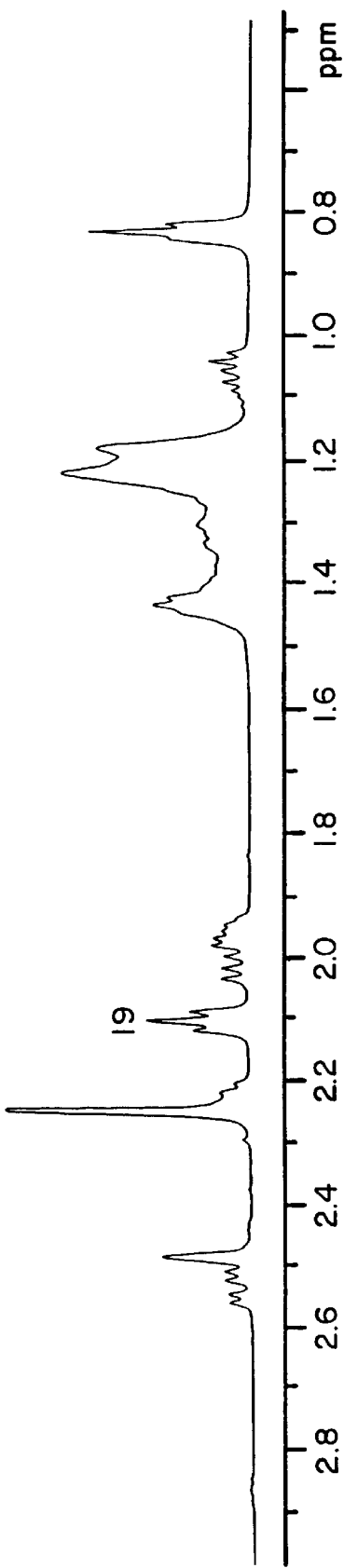

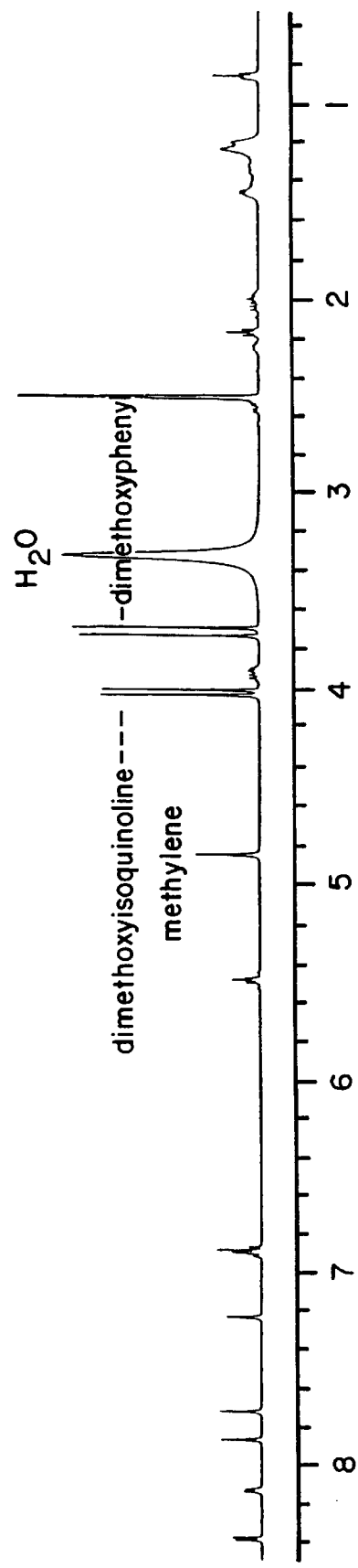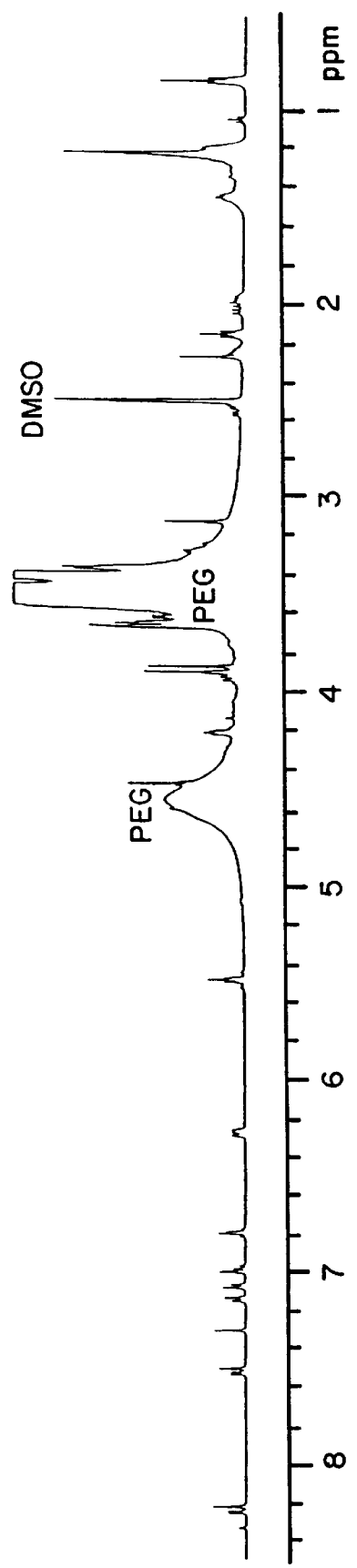
FIG. 3c
FIG. 3d

Phentolamine Mesylate + NaOH →

Reaction 1A

Phentolamine Free Base

Phentolamine Alprostadilate Monohydrate

COMPOUNDS, COMPOSITIONS, AND METHODS FOR TREATING ERECTILE DYSFUNCTION

FIELD OF THE INVENTION

This invention relates to compounds for the treatment of erectile dysfunction, including impotence. In particular, the invention relates to vasoactive compounds and their production, and treatments for impotence and the enhancement of sexual performance in men. The invention also includes a vehicle, delivery system and emulsifier for treating impotence.

BACKGROUND OF THE INVENTION

Erectile dysfunction or impotence is characterized by the inability to achieve or maintain erection or tumescence of the penis. Impotence can be secondary to a wide variety of causes and may be physiological or psychological in origin. This condition is estimated to affect approximately 10–20 million American men chronically, but affects all men occasionally. For example, erection of the penis is inhibited in normal men due to anxiety, exertion or sexual disinterest. Sexual activity includes physical exertion and as men age, the inhibitory effects of exertion may overcome normal arousal mechanisms.

The etiology of chronic impotence may be psychogenic (32%), mixed psychogenic and organic (14%), organic (41%) or anatomical (13%). Organic causes include arterial insufficiency (27%), cavernous leakage (28%), neurological damage (13%), endocrinological defects (2.3%) and Peyronie's disease (13.1%). Govier, F. E. *Timing of Penile Color Flow Duplex Ultrasonography Using a Triple Drug Mixture. J. Urol,* Vol. 153(5) (May 1995), pp. 1472–1475. Thus, about 30% of all cases of impotence are primarily vascular in origin.

Compounds which produce or enhance arterial vasodilation or bring about cavernous vein constriction may be successful for the treatment of impotence. See U.S. Pat. Nos. 5,567,706 and 5,583,144 incorporated by reference. Similarly, compounds which counteract inhibitors of erection, such as catecholamines, may also contribute to effectiveness. Compounds which have been used in the pharmacological induction of erection were the vasodilator papaverine and the catecholamine antagonist, phenoxybenzamine. Such compounds may be administered by injection into the corpora cavernosa of the penis. Brindly, G. S. *Cavernosal Alpha-blockage: A New Technique for Investigating and Treating Erectile Impotence, Br J. Psychiatry,* Vol. 143 (1983), pp. 332. These compounds are thought to work by mimicking the physiological mechanisms that relax penile smooth muscle.

Erection of the penis may be a self-perpetuating process of three steps: 1) vasodilation; 2) release of endogenous smooth-muscle relaxants; and, 3) progression of these effects distal from the initial site of onset. This has been termed the "cascade effect". According to this hypothesis, local induction of vasodilation in the corpus cavernosum may perpetuate itself into full erection of the penis whether or not the original vasodilator diffuses throughout the tissue. Where the concentration of vasoactive drug is highest, there is a local increase in blood flow, an activation of endothelium-mediated relaxing factors such as endothelium-derived nitric oxide, and an enlarging zone of regional smooth muscle relaxation. This "cascade" of a relaxation-inflow-relaxing effect can produce an erection. Support for this hypothesis is found in the observation that high doses of vasoactive drugs are required for erection in impotent patients with endothelial cell dysfunction, such as diabetes and hypercholesterolemia, presumably due to inability of these cells to produce vasodilators. The hypothesis is also supported by the observation that injected vasoactive drugs do not appear to uniformly diffuse from the injection site throughout the corpora of the penis, but are still capable of producing a full erection.

One of the first compounds used successfully for intracavernosal treatment of impotence is papaverine hydrochloride. Papaverine is an opium alkaloid and works as a smooth muscle relaxer possibly by cyclic GMP phosphodiesterase inhibition. It relaxes the musculature of the vascular system of the penis and increases blood flow. The effectiveness of papaverine hydrochloride injection depends on the dose, but has been reported to cause penile hematoma, elevated liver enzymes, priapism and lightheadedness in some patients, particularly if over-used. The free base of papaverine has been tried as a topical agent in the treatment of erectile dysfunction. In concentrations up to 20%, it was not sufficiently effective for clinical use. Kim, E. D. *Papaverine Topical Gel Treatment For Erectile Dysfunction, Urology,* Vol. 133(2)(1995), pp. 361–365.

Another compound found effective in treating impotence is phentolamine hydrochloride or phentolamine methane sulfonate (phentolamine mesylate), described in U.S. Pat. No. 2,503,059 incorporated by reference. Phentolamine free base is a nonspecific alpha-adrenergic antagonist and has been successful in inducing penile erection, particularly when used in combination with papaverine. This combination was found to produce greater vasodilation of the arteries of the penis than either phentolamine or papaverine used alone.

Another compound found useful in the treatment of impotence is prostaglandin $E_1$, a naturally occurring compound that acts to increase arterial inflow to the penis and may also restrict venous outflow. Prostaglandin $E_1$ is preferred to other compounds used in injections for the treatment of impotence because it is metabolized locally in the penis and is less likely to cause systemic symptoms such as hypotension. Further, use of prostaglandin $E_1$ has been found to result in a significantly lower incidence of penile hematomas from injections than either papaverine or phentolamine. However, prostaglandin $E_1$ is considerably more expensive than other therapies and causes pain distal from the site of injection.

A synthetic form of prostaglandin $E_1$, alprostadil USP (alprostadil), is a long-chain carboxylic acid with vasodilatory effects. Alprostadil acts to increase arterial inflow to the penis. In vitro studies have shown that alprostadil causes a dose-dependent smooth muscle relaxation in isolated corpus cavernosum and corpus spongiosum preparations. When used in vivo, it is thought that intraurethral alprostadil is absorbed from the urethra, transported throughout the erectile bodies of the penis by way of communicating vessels between the corpus spongiosum and corpus cavernosum, and induces vasodilation of the targeted vascular beds.

Various forms of alprostadil are available on the market, such as CAVERJECT (Upjohn, Kalamazoo, Mich.), which is an injectable form of alprostadil. Another form of alprostadil is MUSE (Vivus, Inc., Menlo Park, Calif.) which is a combination of alprostadil and polyethylene glycol. Intraurethral administration of MUSE has been reported to result in a substantial increase of cavernosal artery diameter and as much as a 10-fold increase in peak systolic flow velocities. Injections of alprostadil have been reported to cause pain, bleeding, hematomas and scar tissue leading to Peyronie's Disease in some patients.

Urethral inserts or suppositories have been developed as an alternative to intracavernousal injection therapy. For example, U.S. Pat. No. 5,242,391, incorporated by reference, describes a device for the urethral insertion of a pellet containing alprostadil. The device has been reported to be effective about 65% of the time in doses of 125 to 1000 micrograms of alprostadil. However, urethral inserts do not appear to be as successful in treating impotence as intracavernousal injections.

The urethra is sensitive to irritants. There have been some reports that local anesthetic agents such as procaine and lidocaine can relieve some of the irritation upon intracavernousal injection. Schouman, M., *Suppression of Prostaglandin E-1 Induced Pain By Dilution of the Drug With Lidocaine Before Intracavercousal Injection, J. Urology,* Vol 148 (1992), pp.1266.

Androgenic steroids may also have a role in induction of erection, especially for patients with hypogonadism. Dihydrotestosterone has been administered transdermally, but has never been administered intraurethrally. Because dihydrotestosterone is fat-soluble, this may be a reasonable route of delivery. Tostain, J., *Androgen Treatment of Erectile Dysfunction: When?How? Progres en Urologie,* Vol. 7 (1997), pp. 314–319.

Combinations of papaverine, phentolamine and alprostadil have been shown to be effective in treating impotence. For example, intracavernousal injections of this three-way combination, known as "tri-mix", can be more effective in treating impotence with fewer side effects than papaverine, phentolamine or alprostadil used alone. Together, these compounds appear to act synergistically to increase arterial inflow, dilate sinusoidal smooth muscles, and restrict venous outflow, all promoting erectile activity with greater success and in smaller doses than single compound therapies. An example of a dosage combination for tri-mix is 10 micrograms of alprostadil, 500 micrograms of phentolamine and 15 mg of papaverine. Dosing of tri-mix preparations has not been standardized.

Agents for the formation of cationic liposomes are known to increase the solubility of substances they contain in cell membranes. Cationic phospholipids have been described for this purpose, such as phosphatidylethanolamine and phosphatidylcholine. Medium chain fats are useful for the solubilization of chemicals in membranes because they are both fat and water soluble. Therefore, diacylphosphatidylcholine, where the acyl groups are medium chain fats, may be especially efficacious as an emulsifier to aid the uptake of organic compounds by cell membranes. Dilauroylphosphatidylcholine has been disclosed as an ingredient in a composition to form cationic liposomes, for example, in U.S. Pat. No. 5,552,157, incorporated by reference. In the invention, cationic liposomes may form spontaneously when a composition as described is mixed with moisture from the urethra.

SUMMARY OF THE INVENTION

The effectiveness of compositions for the transurethral treatment of impotence depends largely on the chemical nature of the active ingredients and their ability to traverse cell membranes of the urethra and increase blood flow into the corpora cavernosa of the penis. An important factor is fat solubility, which allows diffusion across cell membranes. The invention provides compounds which can be used alone or together for the treatment of erectile dysfunction, particularly impotence. The invention is concerned with compounds that are useful in the treatment of impotence, particularly when delivered to the urethra. The compounds are formed as a complex or reaction product of components in which the lipophobic properties of one or more components are mitigated by formation of the compound. Formation of a compound, as opposed to a mixture of components, can be detected for example by NMR spectroscopy. Methods of making and using these compounds are also disclosed, as is an improved vehicle and delivery system.

The compounds of the invention each comprise a complex or reaction product of an anionic or negatively charged vasoactive or erection-inducing component and a cationic or positively charged vasoactive or erection-inducing component. These components are combined as acids and bases to form compounds which are believed to be organic salts or ionically bonded compounds. One or more compounds of the invention can be used in a composition for treating erectile dysfunction, with or without other ingredients. In a preferred composition, a compound of the invention is combined with a pharmaceutical vehicle and preferably includes an emulsifier. An emulsifier is provided to increase solubility in the mucous membrane of the urethra and can be a form of lecithin, or a compound of the general formula diacylphosphatidylcholine, where the "acyl" portion might include any medium-to-long chain carboxylic acids six to twelve carbons in length. The preferred emulsifier is dilauroylphosphatidylcholine. A local anesthetic may also be included. Preferred anesthetics are lidocaine, also called xylocaine. Preferred compositions may also include more than one compound of the invention.

The compounds of the invention can be represented by the formula:

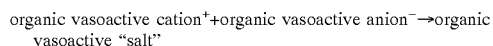

organic vasoactive cation$^+$+organic vasoactive anion$^-$→organic vasoactive "salt"

The organic cation is selected from any of the following vasoactive compounds as the free base: phentolamine, papaverine, hydralazine, ketanserin, delquamine (delaquamine), trazaodone, yohimbine, linsidomine, molsidomine, ifenprodil, piribedil, dipyramidole, minoxidil, phenoxybenzamine, prazocin, terazocin, doxazocin, sildenafil or moxisylyte (moxisylate), or local anesthetics such as procaine or lidocaine free base. The organic anion is selected from any of the following as free acids: vasoactive eicosanoids such as the free acid alprostadil (prostaglandin $E_1$), prostaglandin $E_0$, (13, 14-dihydroprostaglandin $E_1$), dinoprostone (prostaglandin $E_2$), epoprostenol (prostacyclin, $PGI_2$) and other prostaglandins; or other vasoactive anions such as nitroprusside.

One compound of the invention is a combination of alprostadil (an acid) and phentolamine (a base). Another compound of the invention is a combination of alprostadil and papaverine (a base). Each compound of the invention is each believed to form as an ionically bonded salt of its acid and base components. The compounds have the surprising property of high solubility in drug delivery vehicles and lipids, and can easily diffuse across transitional epithelia cells of the urethra. Also, the compounds are benign and effective without undesirable side effects. In a preferred embodiment, compounds of the invention are formulated with an emulsifier, preferably dilauroylphosphatidylcholine, with or without a local anesthetic, such as lidocaine, also known as xylocaine.

The compounds and compositions of the invention can be administered by intraurethral injection or by application to the surface of the penis in the form of a topical composition or agent for transdermal delivery to the urethra.

The compounds and compositions of the invention provide improved solubility, and allow for self-adjusted dosage while preventing overdose problems. In one embodiment, a composition comprising a complex of alprostadil with each of papavarine and phentolamine provides for lower effective doses of alprostadil than in other therapies. This is thought to be achieved by increasing the absorption efficiency, by delivering the composition intraurethrally and by providing a more lipophillic composition which can cross membrane barriers more easily. Thus, alprostadil complexes with papavarine to form the compound papavarine alprostadilate. Alprostadil complexes with phentolamine to form the compound phentolamine alprostadilate.

Surprisingly, the new compounds have synergistic erection-inducing properties, and require significantly less alprostadil component than previously known intraurethral or multi-component intracavernosal therapies. The phentolamine and papaverine moieties are thought to provide alpha-adrenergic blockage and phosphodiesterase inhibition. Additionally, they each neutralize the acidity of alprostadil, rendering the resulting compounds, which can be thought of as salt complexes, fat soluble. Compositions of the invention, comprising one or more compounds formed as the reaction product of acid and base components having erection-inducing properties, have a neutral pH of about 6.0. Alprostadil is acidic, and known alprostadil compositions have an acid pH of about 4.5–5.2 (e.g. for various dosages of MUSE). Further, the anhydrous formulation of phentolamine alprostadilate and papaverine alprostadilate in the presence of an emulsifier, such as dilauroylphosphatidylcholine, ensures that the compounds remain at a neutral pH and in solution as an emulsion upon contact with the neutral aqueous environment of the urethra. The micro droplets which make up this emulsion may directly solubilize in the transitional epithelium of the urethra or the constituents may disassociate by an ion exchange process.

The active ingredients of the composition are provided at significantly lower concentrations than in the prior art. For example, preferred embodiments of the invention provide an effective amount of alprostadil, as phentolamine alprostadilate or papavarine alprostadilate, that can be one-tenth the concentration of alprostadil provided in the commercially available preparation known as MUSE. Consequently, even if compounds or compositions of the invention are self-administered beyond recommended dosage or schedule, the holding capacity of the human urethra will limit dosage to a safe amount. Further, in contrast to needle injections, which deposit the active drug at only one point, intraurethral administration allows diffusion across the urethral membrane all along the line of its path through the cavernosa. This may be another factor which explains why smaller doses of papaverine and phentolamine are effective at inducing erection intraurethrally in comparison to intracavernousally.

BRIEF DESCRIPTION OF THE DRAWINGS

In the drawings, which constitute part of this application, embodiments and data demonstrating various features of the invention are set forth as follows:

FIG. 1a is the NMR spectrum of alprostadil;

FIG. 1b is the NMR spectrum of a compound of the invention, phentolamine alprostadilate;

FIG. 2a is an enlarged view of FIG. 1a, showing the NMR spectra of alprostadilate;

FIG. 2b is an enlarged view of FIG. 1b, showing the NMR spectra of phentolamine alprostadilate;

FIG. 3a is the NMR spectra of alprostadil, as in FIG. 1a;

FIG. 3c is the NMR spectra of a mixture of papaverine hydrochloride and alprostadil;

FIG. 3d is the NMR spectra of a mixture of phentolamine alprostadilate and papaverine alprostadilate in polyethylene glycol, as in FIG. 1e;

DETAILED DESCRIPTION OF THE INVENTION

Figure 1C:
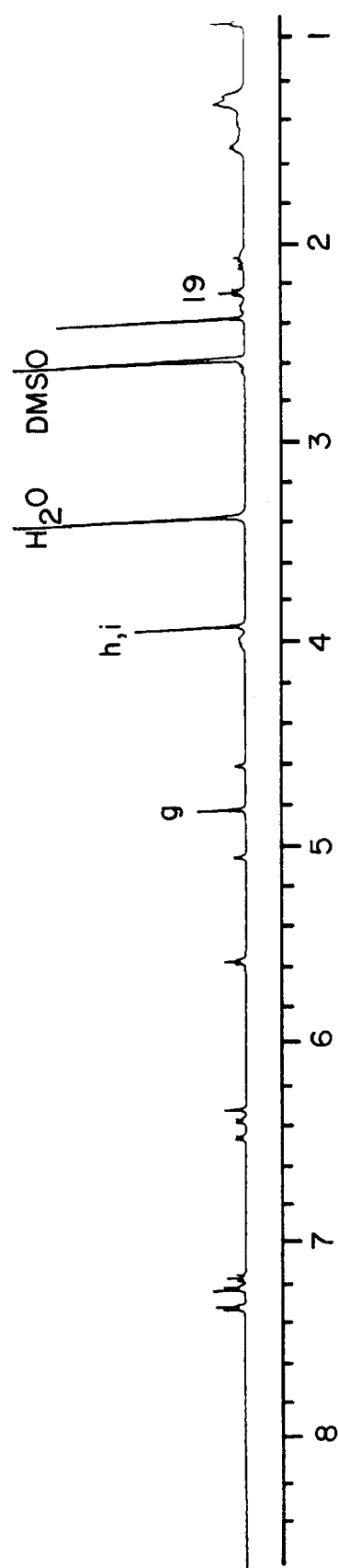
FIG. 1c is the NMR spectrum of alprostadil mixed with phentolamine mesylate.

The compounds of the invention are erection-inducing compounds formed as the stable reaction product of an organic vasoactive cationic moiety, having a positive ionic charge, with an organic vasoactive anionic moiety, having a negative ionic charge. The cationic moiety can also be thought of as a base, the anionic moiety can be thought of as an acid, and the reaction product can be thought of as a "salt" or a "complex."

The organic cation component is selected from any of the following vasoactive compounds as the free base: phentolamine, papaverine, hydralazine, ketanserin, delquamine (delaquamine), trazaodone, yohimbine, linsidomine, molsidomine, ifenprodil, piribedil, dipyramidole, minoxidil, phenoxybenzamine, prazocin, terazocin, doxazocin, sildenafil or moxisylyte (moxisylate), or local anesthetics such as procaine or lidocaine free base.

The organic anion component is selected from any of the following as free acids: vasoactive eicosanoids such as the free acid alprostadil (prostaglandin $E_1$), prostaglandin $E_0$, (13, 14-dihydroprostaglandin $E_1$), dinoprostone (prostaglandin $E_2$), epoprostenol (prostacyclin, $PGI_2$) and other prostaglandins; or other vasoactive anions such as nitroprusside.

The free anion or acid and the free cation or base are mixed, typically in equimolar amounts, in a suitable solvent and the reaction product is crystallized by chilling and adding a solvent or vehicle in which the product is not soluble. Alternatively, the free anion and free cation may be combined in a suitable vehicle for direct use rather than crystallized separately.

Two preferred compounds of the invention are described in detail: phentolamine alprostadilate and papaverine alprostadilate. These compounds are useful for the treatment of erectile dysfunction.

Phentolamine Alprostadilate

Phentolamine alprostadilate has the following chemical structure.

Formula I

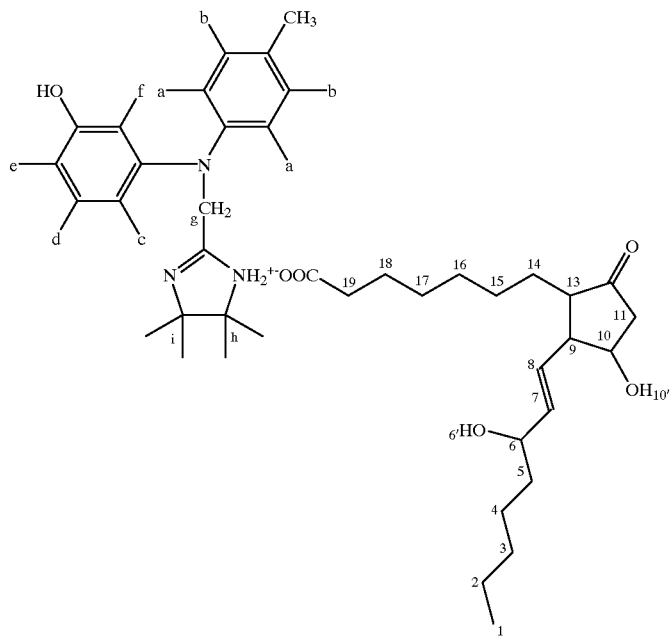

The notations a, b, c, d, e, f, g, h, and i specify protons corresponding to peaks in the NMR spectra of FIGS. 1 and 2. This compound has a molecular formula of $C_{37}H_{53}N_3O_6$ and a molecular weight of 635.84. A solid at room temperature, phentolamine alprostadilate is formed as an off-white waxy flake with a melting temperature of 65–68° C. Phentolamine alprostadilate may be recrystallized by the addition of diethylether to an ethanol solution at −78.5° C., the temperature of a dry ice acetone bath.

Phentolamine alprostadilate is a compound, and is not a mixture of its organic acid and base starting materials. This is shown by nuclear magnetic resonance (NMR) spectra. NMR experiments were performed in the solvent perdeuterodimethylsulfoxide (DMSO) on a Varian Unity Plus 500 spectrometer at 30° C. FIGS. 1a–1e show the proton NMR spectra of alprostadil alone (FIG. 1a), phentolamine alprostadilate (FIG. 1b), a mixture of phentolamine mesylate and alprostadil (FIG. 1c), phentolamine free base alone (FIG. 1d) and a preferred therapeutic composition (a mixture of papaverine alprostadilate and phentolamine alprostadilate with an emulsifier) in polyethylene glycol (FIG. 1e).

Figure 1D:
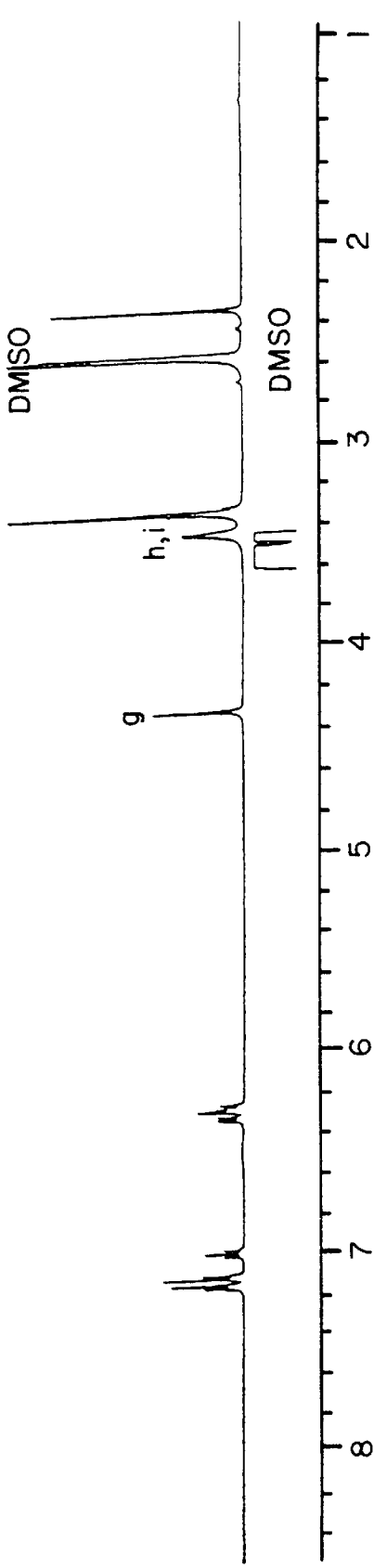
FIG. 1d is the NMR spectrum of phentolamine free base.
Figure 1E:
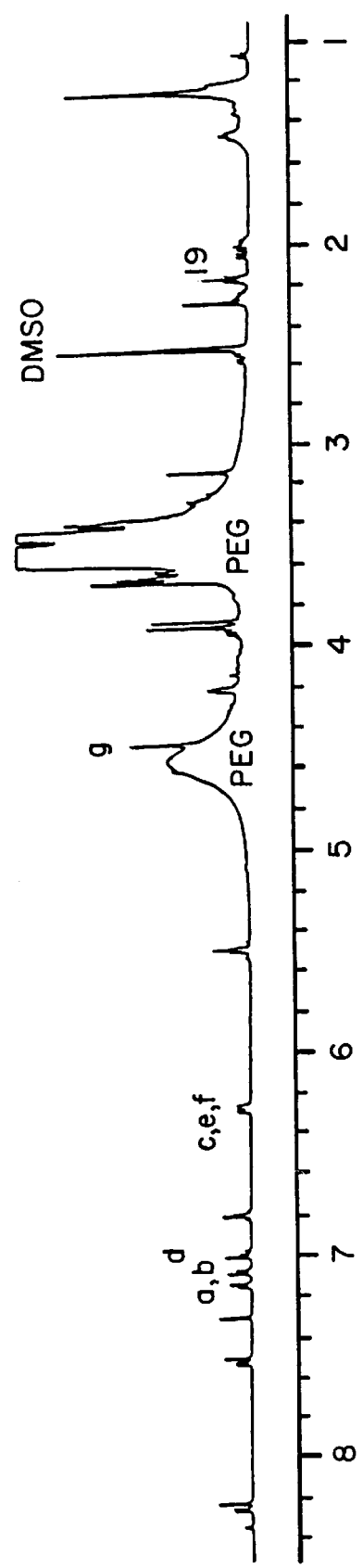
FIG. 1e is the NMR spectrum of a mixture of phentolamine alprostadilate and papaverine alprostadilate in polyethylene glycol.

In FIG. 1a, proton resonance assignments were made as shown using correlated spectroscopy (COSY). The peaks show the proton resonances of the compound alprostadil, which has a molecular formula $C_{20}H_{34}O_5$. In FIG. 1b, the NMR spectrum of phentolamine alprostadilate shows a moderate deshielding of protons g, h and i compared to the free base. These are nearest the ionic bond, as shown in Formula I above and in reactions $1_A$ and $2_A$ of FIG. 4. By comparison with the other figures, this NMR spectrum shows that phentolamine alprostadilate is not the mixture of FIG. 1c. FIG. 1c shows an NMR spectrum of an equimolar ratio of phentolamine mesylate and alprostadil. The down field shift of g, h and i in FIG. 1c is consistent with the fact that mesylate is a stronger acid and therefore a stronger deshielder than alprostadil. Mesylate is the currently marketed drug form of phentolamine, for example, phentolamine mesylate is found in Regitine (Novartis). FIG. 1d shows the NMR spectrum of phentolamine free base, which has the most up field resonances of protons g, h and i. FIG. 1e shows the NMR spectrum of a preferred composition (a mixture of alprostadilate and phentolamine alprostadilate with an emulsifier). The resonances of the g and c, e, f protons is consistent with phentolamine alprostadilate in FIG. 1b showing that this compound persists in the composition.

Figure 2C:
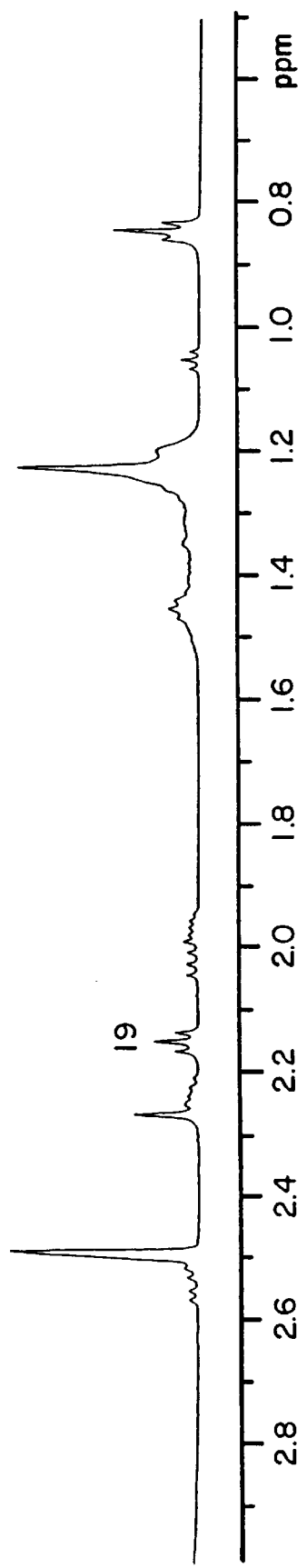
FIG. 2c is an enlarged view of FIG. 1e, showing the NMR spectra of a mixture of phentolamine alprostadilate and papaverine alprostadilate in polyethylene glycol.

FIG. 2a shows the NMR spectrum of FIG. 1a for alprostadil alone, with a close-up view of the triplet resonance assigned to the protons at 19, nearest to the ionic bond of alprostadil. A 0.1 ppm up field shift of proton resonances assigned to position 19 in the close-up spectrum for phentolamine alprostadilate (FIG. 2b) relative to alprostadil (FIG. 2a) was consistent with increased electron shielding due to the formation of an ionic bond at carbon 20 (Formula I). In FIG. 2c, this shift was prevented in the mixture of phentolamine mesylate and alprostadil, apparently because the methanesulfonic acid prevents ionic bond formation between alprostadil and phentolamine. In the close-up of FIG. 2c, the position of 19 is intermediate, because the composition of FIG. 2c is an equimolar mixture of phentolamine alprostadilate and papaverine alprostadilate in polyethylene glycol. The proton resonances at a, b, c, d, e and f in FIG. 1e are also consistent with those in phentolamine alprostadilate shown in FIG. 1b. The proton resonances in FIG. 2c are deshielded to a degree proportional to the acidity of the anion in the ionic bond. The placement of the ionic bond at the imidazole nitrogen(s) is consistent with the deshielding observed at positions g, h and i. These data are also consistent with the infrared absorbance maxima in Nujol which shows hydroxyl (3175 cm$^{-1}$), carbonyl on a 5-member ring (1738 cm$^{-1}$), carboxylate anion (1600 and 1377 cm$^{-1}$) and $NH_2^+$ (1461 cm$^{-1}$).

Theoretical percent composition of phentolamine alprostadilate was estimated to be C:69.89%; H:8.402%; N:6.6085%; remainder [0] 15.0975%. Elemental analysis (Galbraith Laboratories, Knoxville, Tenn.) showed actual percent composition of the compound as C:68.34%; H:8.47%; N:6.54%; and remainder [0]:16.65%. These results were most consistent with a monohydrate.

These results show that phentolamine alprostadilate monohydrate is a compound with the molecular formula $C_{37}H_{55}N_3O_7$ and molecular weight 653.86, as shown in FIG. 1.

Papaverine Alprostadilate

Another effective therapeutic composition for transurethral induction of erection of the penis is papaverine alprostadilate, which has the following chemical structure.

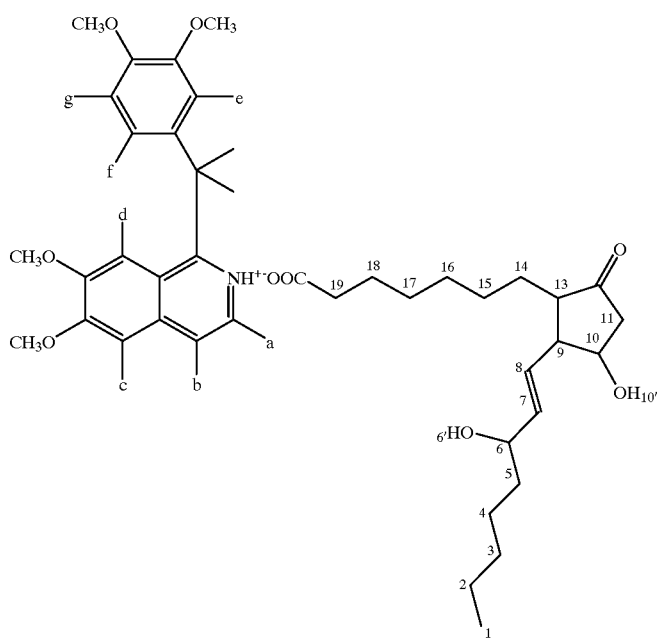

Formula II

The notations a, b, c, d, e, f, and g specify protons corresponding to peaks in the NMR spectra of FIG. 3. This compound has the molecular formula $C_{40}H_{55}NO_9$ and a molecular weight of 693.8. It is a white crystalline solid at room temperature with a melting point of 104–105° C. The UV spectrum of papaverine alprostadilate in ethanol shows maxima at 236 nm (log $\epsilon$4.886), 280–282 nm (log $\epsilon$3.398), 314 nm (log $\epsilon$3.149) and 328 nm (log $\epsilon$3.219).

Figure 3A:
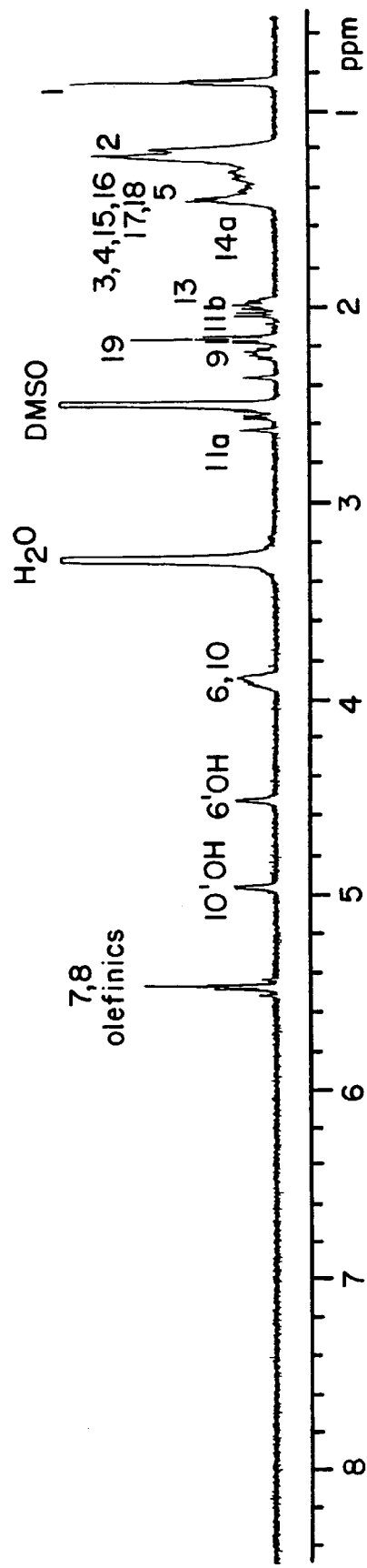
Figure 3B:
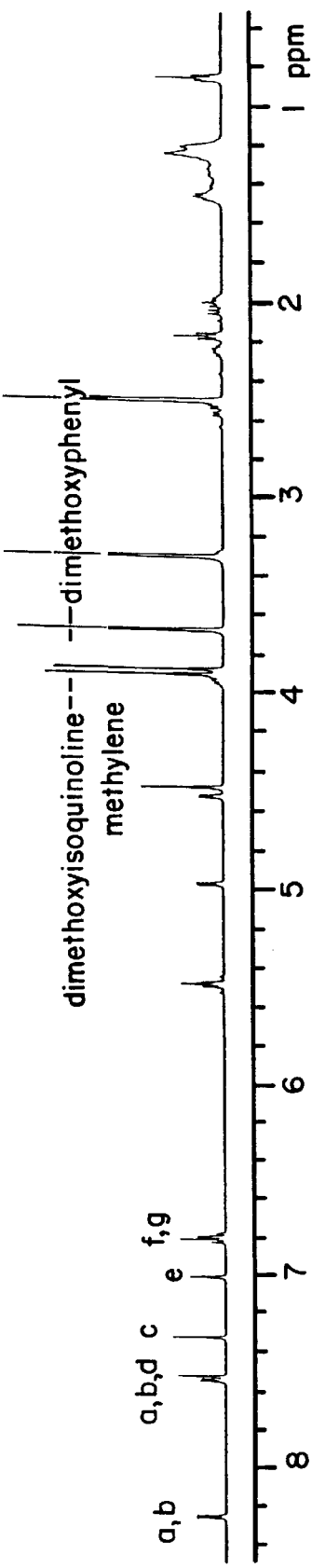
FIG. 3b is the NMR spectra of papaverine alprostadilate.
Figure 4A:
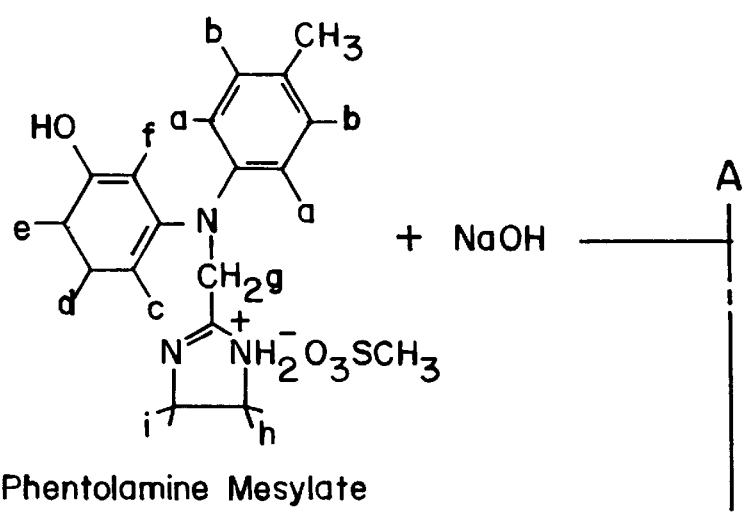
FIG. 4 shows a reaction scheme for the formation of phentolamine alprostadilate.
Figure 4A:
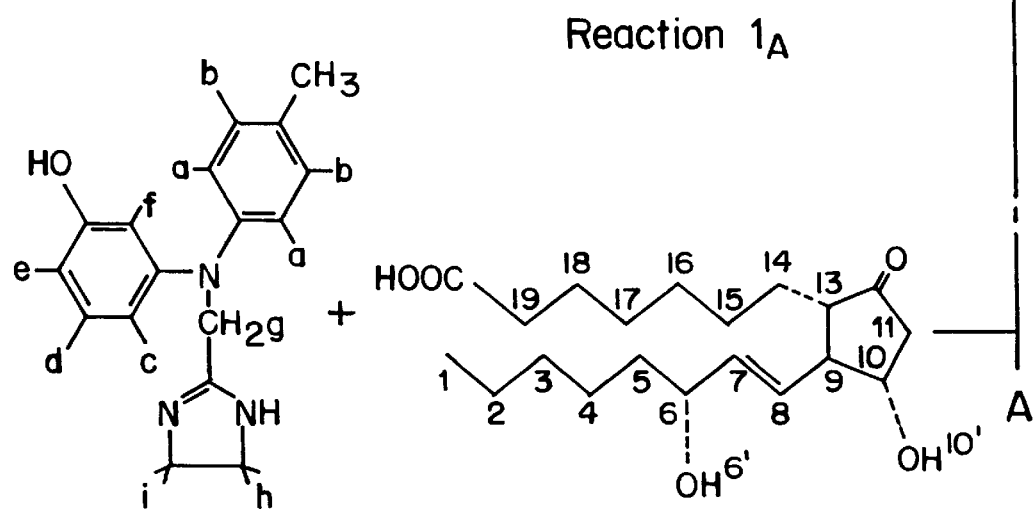
Figure 4B:
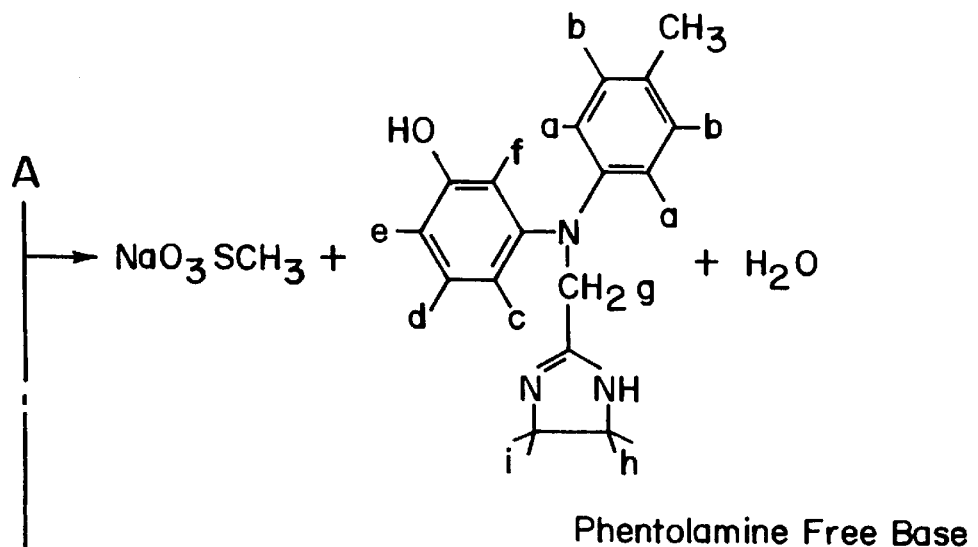
Figure 4B:
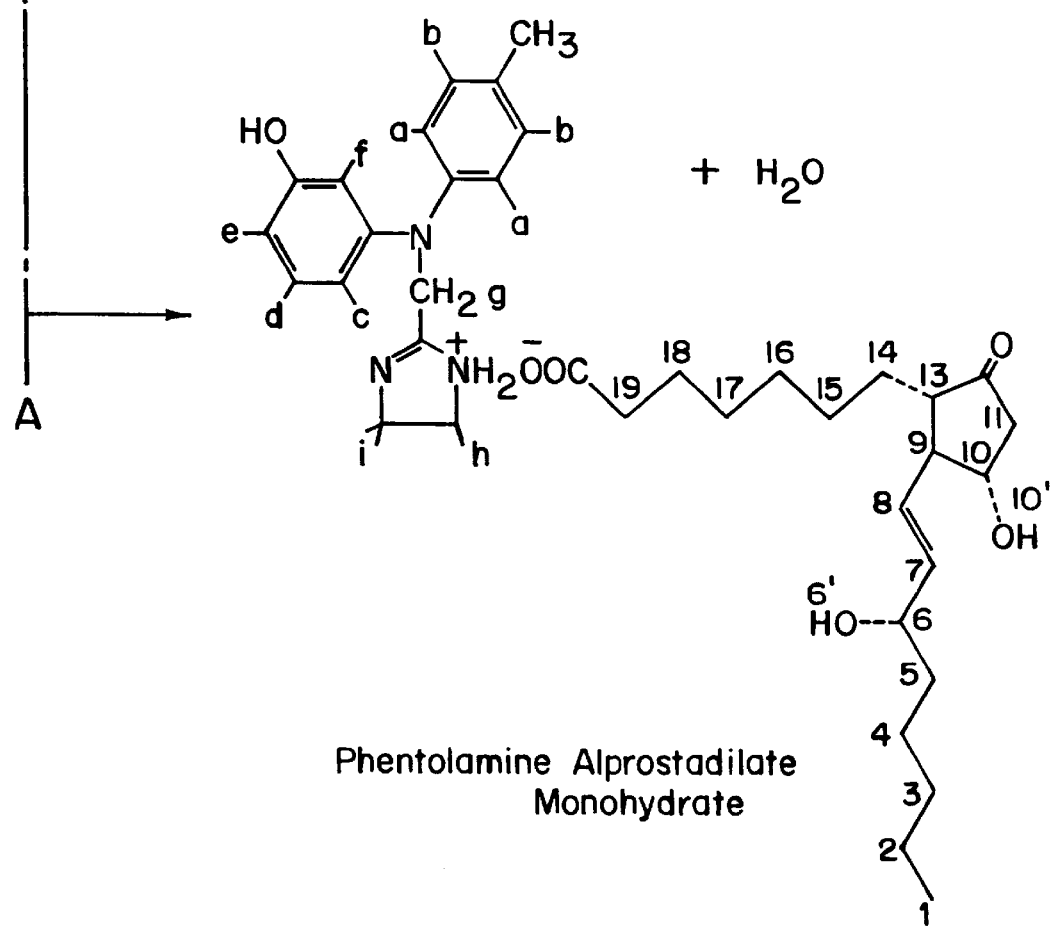

The proton NMR spectra of alprostadil and papaverine alprostadilate and various mixtures of compounds with papaverine alprostadilate are shown in FIGS. 3a–3d. These NMR spectra were obtained on a Varian Unity Plus 500 at 30° C. with a proton resonance frequency of 500 MHz in perdeutero DMSO. FIG. 3a shows the NMR spectrum of alprostadil alone with the various peaks labeled according to the numbers shown in the structure of Formula II for papaverine alprostadilate. FIG. 3b shows the NMR spectrum of papaverine alprostadilate. A nuclear overhauser effect (NOE) experiment demonstrated through-space interactions between protons d and e, f, g (FIG. 3b). This suggests that the dimethoxyphenyl group is constrained as shown in FIG. 3b by the presence of the bulky alprostadilate anion. The structural differences between alprostadil and papaverine alprostadilate are apparent by examining the NMR spectra of alprostadil and papaverine alprostadilate. Note that the peaks a, b, c, d, e, f and g correlate to the hydrogens on the phenyl groups which are not present in alprostadil.

FIG. 3c shows an NMR spectrum of an equimolar solution of papaverine hydrochloride and alprostadilate. The large down field shift due to deshielding of the methylene protons which occurred in the equimolar mixture of papaverine hydrochloride and alprostadil was not seen either in the NMR spectra of papaverine alprostadilate, FIG. 3b, or in the complete therapeutic composition, FIG. 3d. As with the compound phentolamine alprostadilate, the NMR spectrum of papaverine alprostadilate confirms that papaverine alprostadilate is a reaction product or compound. It is not merely a mixture of its organic acid and base starting materials, either in its pure form or in the therapeutic vehicle.

Preparation of Phentolamine Alprostadilate

The formation of phentolamine alprostadilate monohydrate by reactions $1_A$ and $2_A$ is shown in FIG. 4. Phentolamine mesylate (Reliable Biopharmaceutical, St. Louis, Mo.) was dissolved in water at a concentration of up to 5 mg/ml (e.g. 3 mg/ml). An equimolar amount of 1 M sodium hydroxide in water was added to the solution. Phentolamine free base, as a white precipitate, was collected by filtration or centrifugation and washed with water. The white precipitate was desiccated overnight in a vacuum desiccator containing phosphorus pentoxide powder resulting in a dry white powder.

Equimolar amounts of the phentolamine free base and alprostadil USP (Chinoin Pharmaceutical and Chemical Works, Ltd., Budapest, Hungary) were dissolved in USP ethanol. The solvent was evaporated in a rotary evaporator at 25° C. and a 20 mm Hg vacuum. Anhydrous diethyl ether was added as the mixture thickened and a white precipitate appeared and increased in mass with chilling in a dry ice acetone bath. Continued removal of solvent yielded a white solid. The white solid was washed with diethyl ether twice and placed overnight in a vacuum desiccator containing phosphorous pentoxide.

Theoretical composition was estimated to be C:69.89%; H:8.402%; N:6.60%; and 0:15.0975%. Elemental analysis of the product (Galbraith Laboratories, Knoxville, Tenn.) showed a composition of C:68.34%, H:8.47%, N:6.54% and 0:16.65%. Ultraviolet absorbance maxima for this compound in methanol were 212 nm (log $\epsilon$4.179) and 218 nm (log $\epsilon$3.597). Infrared absorbance maxima in Nujol was consistent with hydroxyl (3175 cm$^{-1}$), carbonyl on a 5-membered ring (1738 cm$^{-1}$), carboxylate anion (1600 and 1377 cm$^{-1}$ NH$_2^+$ (1461 cm$^{-1}$).

Preparation of Papaverine Alprostadilate

Figure 5A:
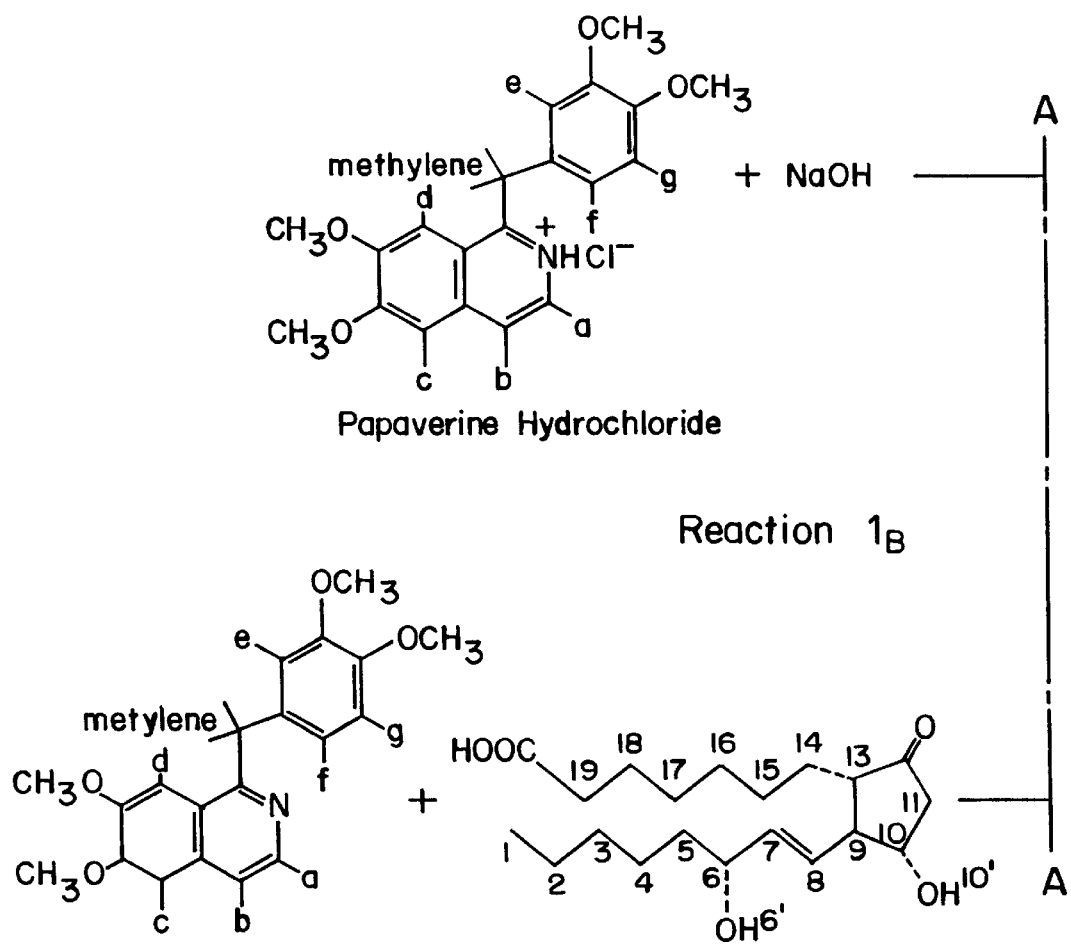
FIG. 5 shows a reaction scheme for the formation of papaverine alprostadilate.
Figure 5B:
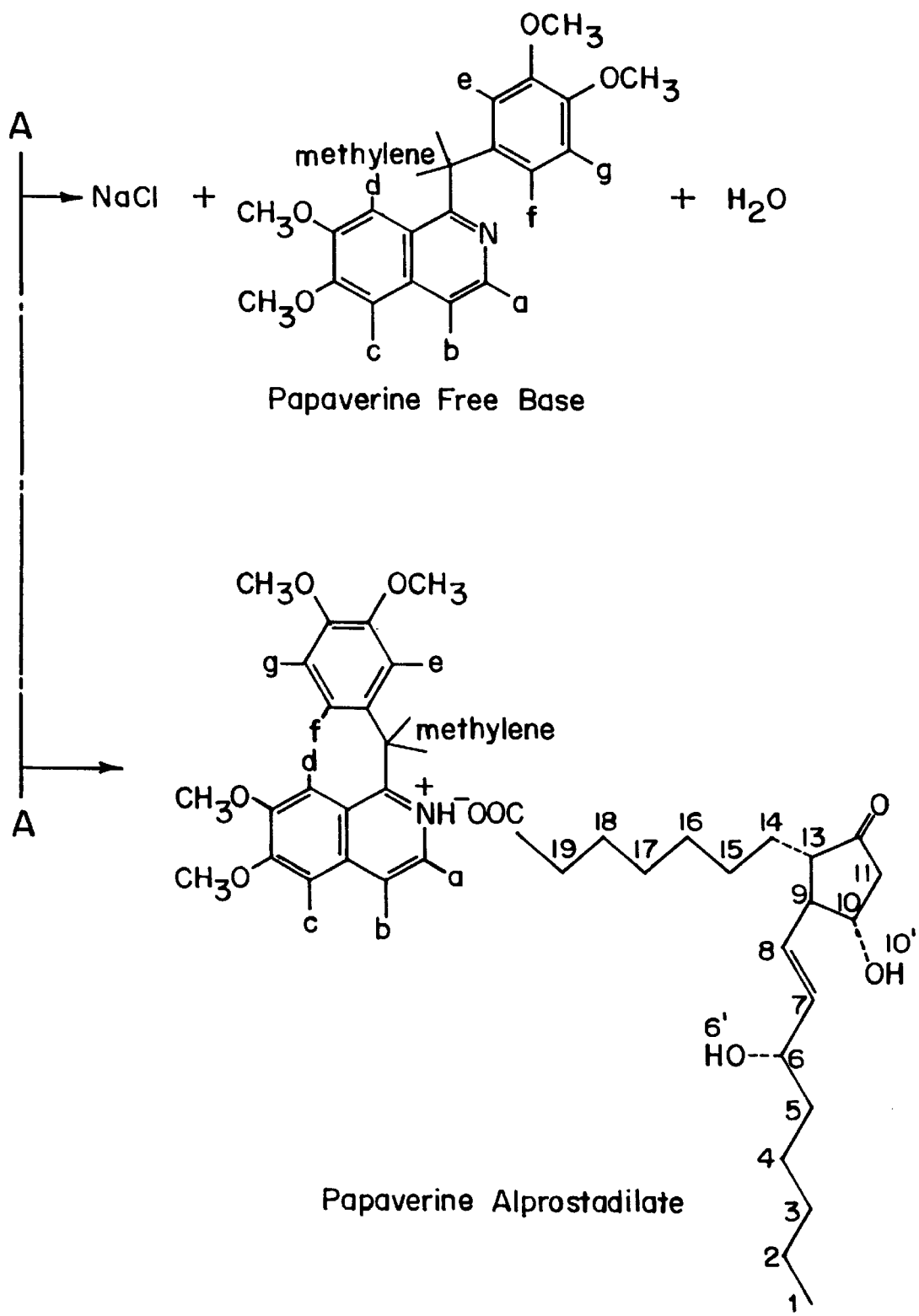

Formation of papaverine alprostadilate from papaverine hydrochloride is shown in FIG. 5. Equimolar amounts of papaverine free base (Lancaster Synthesis, Eastgate, White Lund, Morecambe, England) and alprostadil USP (Chinoin Pharmaceutical and Chemical Works, Ltd., Budapest, Hungary) were dissolved in USP ethanol. The solvent was removed under a nitrogen stream at 70° C. resulting in a clear oil. The clear oil was allowed to stand at 20° C. until crystallized. It was recrystallized from USP ethanol by adding diethylether in a dry ice-acetone bath. The rate of crystallization was increased by seeding with crystals from prior syntheses.

Theoretical elemental analysis was estimated to be C:69.23%; H:7.984%; N:2.02% and remainder [0]:20.75%. Elemental analysis (Galbraith Laboratories, Knoxville, Tenn.) showed an actual percent composition of C:69.26%; H:8.18%; N:1.91% and remainder [0]:20.65%.

EXAMPLE 1

Tri-Mix

A tri-mix formulation was made as follows. In an agate mortar and pestle, alprostadil (Chinoin Pharmaceutical and Chemical Works, Ltd., Budapest, Hungary) as the free acid was mixed as a 2.5% solution of a mixture of warm polyethylene glycol 1000 MW and polyethylene glycol 200 MW at a ratio of 2:1 respectively. A half molar equivalent each of phentolamine mesylate and papaverine hydrochloride was added and the mixture was mixed in the agate mortar and pestle.

The mixture was administered intraurethrally in a dose of 1 mg alprostadil, 0.53 mg phentolamine mesylate and 0.53 mg papaverine hydrochloride of the mixture to a human subject. This treatment induced erection but with the undesirable side effects of dizziness and other symptoms of hypotension. The preparation contained visible undissolved papaverine hydrochloride which caused irritation of the urethra.

For comparison, a common dose of tri-mix used in intracavernousal injections contains from about 200 to about 500 micrograms ($\mu$g) of phentolamine (typically 500 $\mu$g), 2.5 to 60 milligrams (mg) of papaverine (typically 15 mg), and 10–60 $\mu$g of alprostadil (typically 10 $\mu$g). Lidocaine HCl (5%) has also been used. Intraurethrally, alprostadil has been used alone in amounts of from 125–1000 $\mu$g. For example, in a maximum dose of MUSE, 1000 $\mu$g of alprostadil is administered intraurethrally.

EXAMPLE 2

Phentolamine Alprostadilate, Papaverine Alprostadilate and Emulsifier

Per gram of total composition, 22.42 mg phentolamine alprostadilate, prepared according to the method of FIG. 4, was dissolved at 55° C. in a mixture of polyethylene glycol 1000 MW and polyethylene-glycol 200 MW at a ratio of 2:1 respectively, with the addition of 0.005% butylated hydroxytoluene (BHT). Two-thirds of an equimolar amount of dilauroylphosphatidylcholine or 29.2 mg/gm (Avanti Polar Lipids, Birmingham, Ala.) were added to the mixture as an emulsifier. The composition was mixed in an agate mortar and pestle at 55° C. until dissolved. A molar equivalent of 24.5 mg/gm papaverine alprostadilate, made according to FIG. 5, was added and mixed in the mortar and pestle at 55° C. The formulation had a weight ratio of alprostadil to final composition of 1:40 (1000 micrograms of alprostadil as the combined phentolamine and papaverine salts to 40 mg of the final composition). This composition was passed through a sterile 0.2 micron anodized aluminum filter (Anotop 10, Whatman International, Maidstone, England) by syringe at 55° C. to yield a clear, sterile, particle-free preparation. On cooling to room temperature, the composition solidified to a white paste.

EXAMPLE 3

Papaverine Alprostadilate with DHT and Emulsifier 49 mg of papaverine alprostadilate, made by the method of FIG. 5, was dissolved in 935.4 mg of a mixture of polyethylene glycol 1000 MW and polyethylene glycol 200 MW at a ratio of 2:1. 14.6 mg of dilauroylphosphatidylcholine and 1 mg of dihydrotestosterone were added to the mixture.

Intraurethral administration equal to 1000 mg alprostadil was given. Each dose was effective to induce erection in an unaroused human subject with no noticeable side effects and little urethral irritation.

EXAMPLE 4

Phentolamine Alprostadilate, Papaverine Alprostadilate and Emulsifier 36.75 mg of papaverine alprostadilate, 11.2 mg of phentolamine alprostadilate and 7.3 mg of dilauroylphosphatidylcholine were mixed in a warm mortar and pestle. 756 mg of melted 1000 molecular weight polyethylene glycol and 189 mg of 200 molecular weight polyethylene glycol were mixed at a 4:1 ratio respectively and then added to the composition.

This comprised a three-to-one molar ratio of papaverine alprostadilate to phentolamine alprostadilate with a ratio of the total alprostadilate to the vehicle of 1:40 (by weight). The vehicle included dilauroylphosphatidlycholine in a molar ratio of 1:6 to alprostadil.

EXAMPLE 5

Phentolamine Alprostadilate, Papaverine Alprostadilate, Papaverine Free Base and Emulsifier This composition was formulated as in Example 4, but was supplemented with papaverine free base. The addition of the papaverine free base helps neutralize the pH and provide for a less acidic composition. Per gram of the total composition, 11.3 mg of phentolamine alprostadilate, 38.2 mg of papaverine alprostadilate and 10.5 mg of papaverine free base were mixed in 932.7 mg of a vehicle consisting of a mixture of 1000 MW and 400 MW pharmaceutical grade polyethylene glycol (Paddock Labs, Minneapolis, Minn.) at a ratio of 2:1 respectively. 7.3 mg of dilauroylphosphatidylcholine and 0.005% BHT were also added. Papaverine free base can be made by dissolving papaverine HCl USP is deionized water and adding an equimolar amount of sodium hydroxide USP. The resulting precipitate is filtered and dried in a vacuum dessicator containing phosphorous pentoxide. Phentolamine free base can be made by dissolving phentolamine mesylate USP in deionized water and adding an equimolar amount of sodium hydroxide USP. The precipitate is filtered and dried in a vacuum dessicator containing phosphorous pentoxide.

A typical maximum dose of this composition (40 mg) has 198 micrograms of phentolamine free base (molar equivalent of 256.6 micrograms of phentolamine mesylate) and 718 micrograms of papaverine free base (molar equivalent of 795 micrograms of papaverine hydrochloride). The pH of a 1:1 mixture of this composition and water was 5.5. This is in contrast to the current state-of-the-art compounds (MUSE) which gives a pH of 4.5, indicating it is 10 times more acidic.

EXAMPLE 6

Papaverine Alprostadilate, Phentolamine Alprostadilate, Lidocaine Alprostadilate, in Polyethylene Glycol with 0.02% BHT and Excess Papaverine Free Base 18 milligrams butylated hydroxytoluene (BHT) was mixed into 2 grams pharmaceutical grade polyethylene glycol of average molecular weight 400 in an agate mortar and pestle. This was diluted and mixed with 28 more grams of 400 MW PEG and 60 gm of warmed 1000 MW PEG to give a total of 90 grams such that the final concentration of BHT was 0.02%. This comprised the "vehicle." A sufficient quantity of vehicle (927.7 g per g final composition) was used to dissolve the following (per gram of final composition): lidocaine free base, 5 mg (to give a final concentration of 0.5%), phentolamine free base, 5 mg; papaverine free base, 30 mg; alprostadil, 25 mg; dilauroylphosphatidylcholine, 7.3 mg (a 1:6 molar ratio to alprostadil). In preferred compositions the amount of phentolamine free base ranges from 5–10 and the amount of papaverine free base ranges from 30–60 mg. The measured pH of this preparation in a 1:1 mixture with water was 5.9. When 40 mg was administered intraurethrally to an unaroused male, erection resulted within 5 minutes. This composition provided extra papaverine as in Example 5 and xylocaine in a concentration adequate to minimize urethral irritation for the few minutes of its usual duration, without causing numbness of the genitals.

Throughout the examples, alprostadil is provided as the free acid or organic anion. However, other acids or organic anions which may be used in conjunction with papaverine free base and phentolamine free base are: prostaglandin $E_0$ (13, 14-dihydroprostaglandin $E_1$) dinoprostone (prostaglandin $E_2$), epoprostenol (prostacyclin, $PGI_2$) and other prostaglandins, or other vasoactive anions such as nitroprusside. Other vasoactive bases or organic cations which may be utilized with the previously stated acids are: alpha-adrenergic antagonists, hydralazine, ketanserin, delquamine (delaquamine), trazaodone, yohimbine, linsidomine, molsidomine, ifenprodil, piribedil, dipyramidole, minoxidil, phenoxybenzamine, prazocin, terazocin, doxazocin, sildenafil (Viagra) or moxisylyte (moxisylate), or other basic c-GMP-phosphodiesterase inhibitors likely to form salts with carboxylic acids or local anesthetics such as procaine or lidocaine free base.

The free acids and bases are mixed in equimolar amounts in a suitable solvent and crystallized by chilling and adding a solvent in which the product is not soluble by the same general methods as provided in the examples.

The formulations of Examples 1–6 are summarized in Table I, below.

TABLE I

| EX. # | Components | Amount (mg/g) | Molar Ratio | Free Acid or Base Equivalent (mg/g) | | Max.Dose (µg) | Comments | Vehicle (Ratio of PEG 1000:PEG 200) |
|---|---|---|---|---|---|---|---|---|
| 1 | alprostadil | 25.0 | 2 | alprostadil | 25 | 1000 | Lightheadedness, diaphoresis, undissolved papaverine, pronounced urethral irritation. | Ratio of PEG (1000 mw) to PEG (200 mw) is 2:1; |
|  | papaverine HCL | 13.25 | 1 | papaverine | 12.0 | 480 |  |  |
|  | phentolamine mesylate | 13.40 | 1 | phentolamine | 10.0 | 400 |  |  |
| 2 | papaverine alprostadilate | 24.5 | 3 | alprostadil | 25.1 | 1000 | Symptoms of hypotension. Components dissolved satisfactorily; some urethral irritation | 0.005% BHT |
|  | phentolamine alprostadilate | 22.42 | 3 | papaverine | 10.8 | 430 |  |  |
|  |  |  |  | phentolamine | 11.0 | 438 |  |  |
|  | DLPC | 14.6 | 2 | DLPC | 14.6 |  |  |  |
| 3 | papaverine alprostadilate | 49.0 | 3 | alprostadil | 25 | 1000 | Some urethral irritation. |  |
|  |  |  |  | papaverine | 24 | 960 |  |  |
|  | DHT | 1.0 | — | DHT | 1.0 | 40 |  |  |
|  | DLPC | 14.6 | 1 | DLPC | 14.6 |  |  |  |
| 4 | papaverine alprostadilate | 36.75 | 6 | alprostadil | 25 | 1000 | Less adhesive to catheter; some urethral irritation. No hypotension with lower dose of phentolamine; | Ratio of PEG (1000 mw) to PEG (200 mw) is 4:1; 0.005% BHT |
|  | phentolamine alprostadilate | 11.2 | 2 | papaverine | 18 | 720 |  |  |
|  |  |  |  | phentolamine | 5 | 200 |  |  |
|  | DLPC | 7.3 | 1 | DLPC | 7.3 |  |  |  |
| 5 | papaverine alprostadilate | 38.2 | 6 | alprostadil | 25 | 1000 | Much less urethral irritation (pharmaceutical grade PEG); overall pH 5.5 | Ratio of PEG (1000 mw) to PEG (400 mw) is 2:1; 0.02% BHT |
|  | phentolamine alprostadilate | 11.3 | 2 | papaverine | 30 | 1200 |  |  |
|  |  |  |  | phentolamine | 5 | 200 |  |  |
|  | DLPC | 7.3 | 1 | DLPC | 7.3 |  |  |  |
| 6 | alprostadil | 25 | 6 | alprostadil | 25 | 1000 | No urethral irritation; overall pH 6.0. | Ratio of PEG (1000 mw) to PEG (400 mw) is 2:1; 0.02% BHT |
|  | papaverine free base | 30 |  | papaverine | 30 | 1200 |  |  |
|  | phentolamine free base | 5 |  | phentolamine | 5 | 200 |  |  |
|  | DLPC | 7.3 | 1 | DLPC |  |  |  |  |
|  | lidocaine free base | 5 |  | lidocaine | 5 | 200 |  |  |
| DLPC: dilauroylphosphatidylcholine | | | DHT: dihydrotestosterone | | BHT: butylated hydroxytoluene | | | |

In the Table, ingredients other than the pharmaceutical vehicle are listed in the Components column. The vehicle is described in the Vehicle column. The weight of each ingredient in mg/g is given in the Amount column, the molar ratios of the ingredients to each other are given in the Molar Ratio column, and the equivalent weight of each ingredient as free acid or base is given in the Equivalent column. The maximum dose of each active ingredient of these exemplary formulations, given in the Max. Dose column, are based on a preferred 40 mg maximum dose of each formulation. Observations concerning each formulation are in the Comments column.

EXAMPLE 7

Delivery System and Dosage Form Packaging

In one embodiment, the composition according to the invention is delivered into the penis by an applicator. An exemplary applicator is made by Custom Medical Concepts, Chelmsford, Mass., from extruded polyethylene catheter tubing in an outer diameter equivalent to 8 French and an inner diameter of 0.050 inches. This applicator is open at both ends and rounded at the distal end into an atraumatic shape known in the art. The proximal end was fitted with a low-dead-volume female luer to 1/16 barb adapter made of KYNAR, which is a hard, white polyvinylidene fluoride resin known for its resistance to chemical erosion and heat. The applicator is designed so that there is no constriction in the inner diameter of the applicator at any point in the path of the composition. The luer is available from Value Plastics in Fort Collins, Colo. The applicators are sealed in suitable packaging required for ethylene oxide sterilization and then sterilized.

Prior to packaging, the composition is passed through a warmed, sterile, 0.2 micron anodized aluminum filter (Anotop 10, Whatman International, Maidstone, England). Premeasured single-use applicators were prepared by drawing up the warmed composition to give the approximate dosages as shown below. Each applicator contained one of the following dosage combinations as marked.

TABLE II

| Marking | Alprostadil ($\mu$g) | Phentolamine ($\mu$g) | Papaverine ($\mu$g) | Total Composition (mg) |
|---|---|---|---|---|
| 250 | 250 | 50 | 300 | 10 |
| 500 | 500 | 100 | 600 | 20 |
| 750 | 750 | 150 | 900 | 30 |
| 1000 | 1000 | 200 | 1200 | 40 |

Alternatively, the composition is passed through a warm, sterile, 0.2 micron anodized aluminum filter (Anotop 10, Whatman, International, Maidstone, England) into a 3 cc syringe or dispenser. The dispenser was previously sterilized by ethylene oxide and lubricated with 200 MW polyethylene glycol containing 0.005% BHT. The dispenser was filled with the composition in a laminar flow hood and inserted and sealed into a sterile wrapper.

The applicator was then fined onto the dispenser and the composition was expressed into the applicator to a proximal mark, for a dose of 500 micrograms of alprostadil equivalent and to a distal mark on the dispenser for 1000 micrograms. The loaded applicator was then detached from the dispenser and attached to a 1 cc syringe. The dispenser-applicator apparatus allowed variable doses to be measured out by the user according to his requirements at the time of use.

In use, the subject first urinated, then the applicator was inserted one inch or less into the urinary meatus, and the composition was deployed by forced air through the syringe by pushing the plunger. Delivery of the effective dose was attended by an audible "pop". The concentrations of the new compositions of matter and emulsifier in the composition were chosen to prevent overdosage at the holding capacity of the human urethra. That is, the concentration of active ingredients in the vehicle was diluted to a point such that the maximum capacity of the urethra would contain a safe dose of active ingredients effectively preventing overdosage. This is in contrast to the prior art compositions which are many times more concentrated and many times the recommended dosage may be injected and held within the urethra.

EXAMPLE 8

Administration of Compounds of the Invention

Figure 6A:
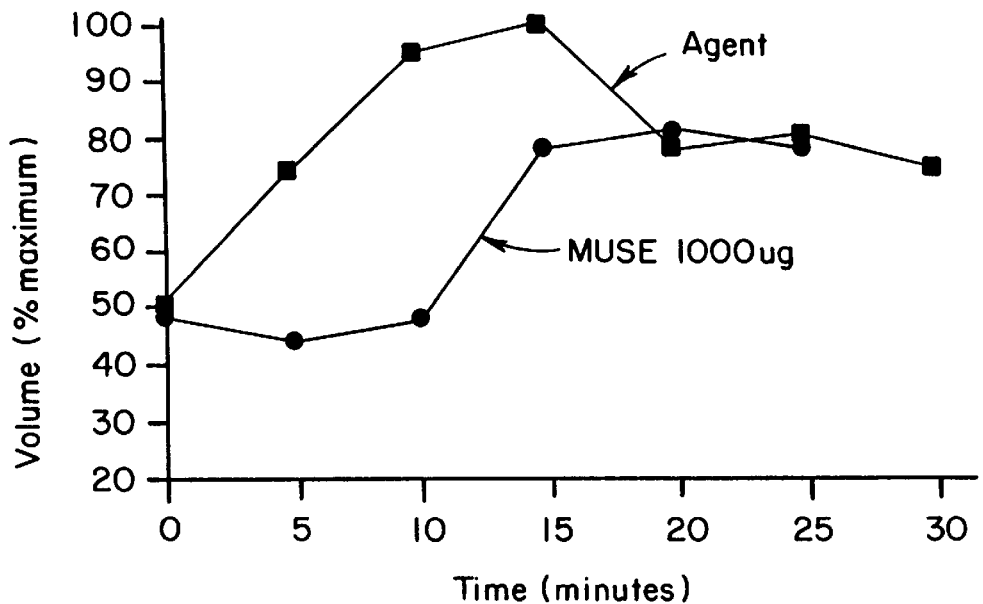
FIG. 6a shows a comparison of increase in penile volume for alprostadil and a composition of the invention, each at a dose of 1000 ug alprostadil equivalent for Subject 1.
Figure 6B:
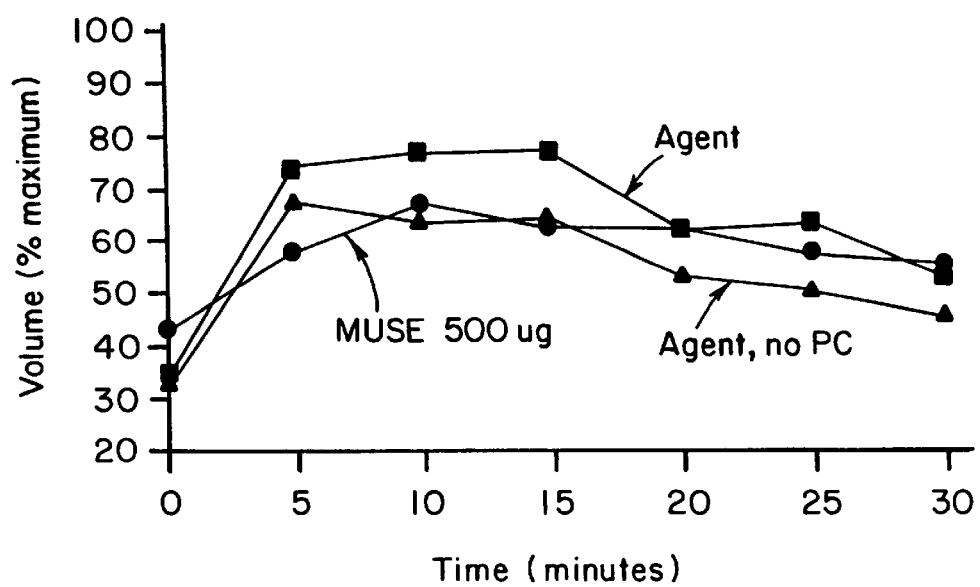
FIG. 6b shows a comparison of increase in penile volume for alprostadil and two compositions of the invention (with and without dilauroylphosphatidylcholine), each at a dose of 500 ug alprostadil equivalent for Subject 1.
Figure 6C:
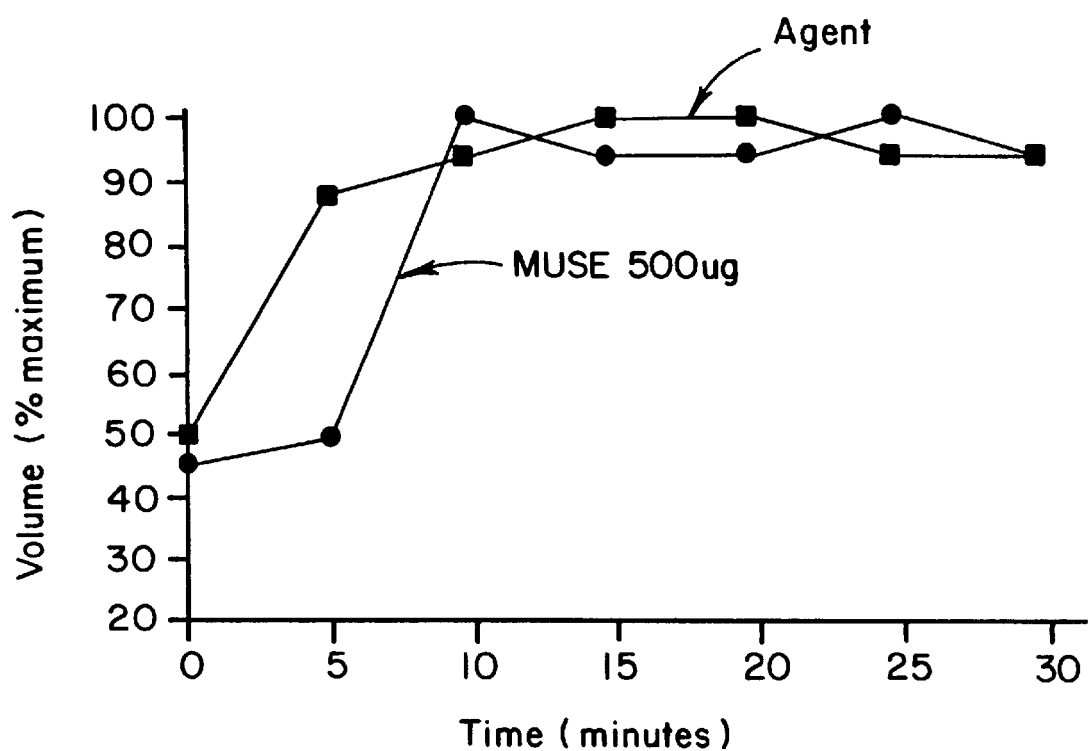
FIG. 6c shows a comparison of increase in penile volume for alprostadil and a composition of the invention, each at a dose of 500 ug alprostadil equivalent for Subject 2.

The composition of Example 4 was compared to alprostadil alone (MUSE) as shown in FIGS. 6a–6c. The subjects first urinated to ensure that there was moisture within the urethra. Penile length was measured and circumference was measured at the corona. Penile volume was estimated by the formula $2\pi r^2 \times length$, by calculating an estimated penile radius from circumference/$2\pi$. Maximum penile volume was determined subjectively by each subject. The subjects self-administered 1000 micrograms of alprostadil equivalent as the composition of Example 4, that is, 40 mg of the total composition, and at another time self-administered 1000 micrograms of alprostadil alone. Every five minutes for thirty minutes, measurements of penile length and circumference were made. As shown in FIGS. 6a–6c, the therapeutic composition produced a faster onset of erection in subjects 1 and 2 than the prior art compounds.

FIG. 6b shows a three-way comparison of alprostadil alone, the composition of Example 4, and the composition of Example 4 without dilauroylphosphatidylcholine. Subject 1 self-administered 500 micrograms of alprostadil, 500 micrograms of composition, and 500 micrograms of the composition without dilauroylphosphatidylcholine. At the lower dose of 500 micrograms, as shown in FIG. 6b, none of the products induced maximum penile volume. However, FIG. 6b demonstrates the effectiveness of the emulsifier, dilauroylphosphatidylcholine, in increasing the efficacy of the therapeutic composition by promoting faster onset of erection. Other potential emulsifiers which can be used are other diacylphosphatidylcholines.

FIG. 6c shows that Subject 2 required only 500 micrograms of alprostadil, or 500 micrograms of the composition of Example 4 to achieve maximum penile volume. As shown by FIG. 6c, the therapeutic composition caused more rapid tumescence of the penis than an equivalent amount of alprostadil (MUSE).

EXAMPLE 9

Topical or Transdermal Delivery

The compositions of the invention can also be applied topically, without a catheter. For example, a composition according to Example 4 and further including known penetration or flux enhancers, such as dimethylsulfoxide (DMSO), glycerol, or glycerol monolaureate, can be applied to the glans penis or to the accessible mucous membranes at the urinary meatus. In one embodiment, a composition was prepared comprising 10% phentolamine alprostadilate and 1% dilauroylphophatidyl choline mixed in a vehicle of 50% 1000 molecular weight PEG, 45% glycerol, and 5% DMSO. An alternative to glycerol in this preparation is glycerol monolaureate. In one experiment, this transdermal preparation was applied to the glans penis and to accessible portions of the urethral mucosa at the urinary meatus, approximately one hour after oral administration of 50 mg of sildenafil. Irritation was minimal, and erection of the penis followed approximately 5 minutes after this transdermal administration of the phentolamine alprostadilate composition.

Although illustrative embodiments are disclosed, other suitable embodiments for practicing the invention may be employed and will be apparent to persons of ordinary skill in the art. The particular compounds, production methods and treatments disclosed are exemplary, and it is to be understood that the scope of the invention is to be determined according to the claims.

We claim:

1. A compound of the following structure:

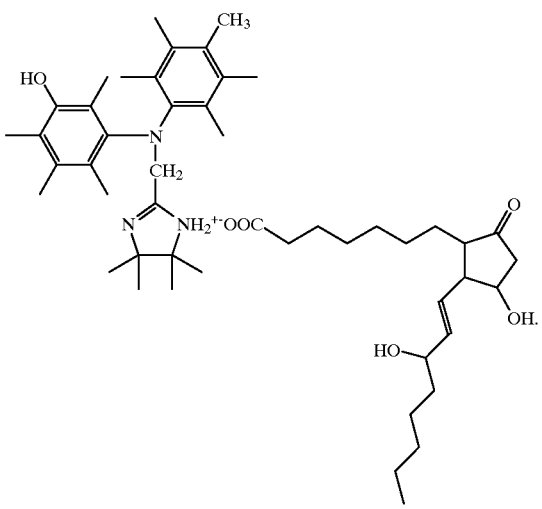

2. A compound of the following structure:

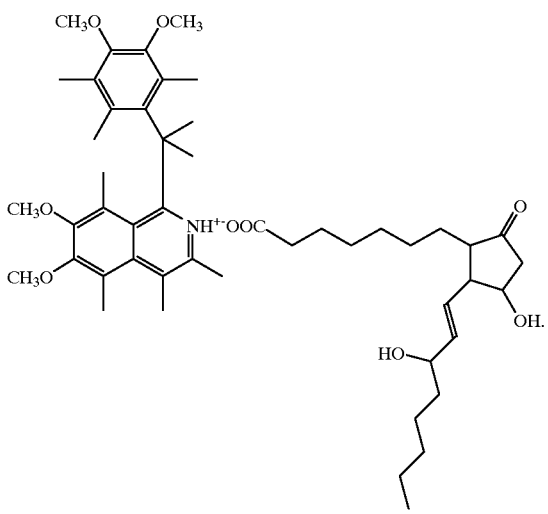

3. A method of producing phentolamine alprostadilate comprising the steps of:
    dissolving a quantity of phentolamine in water to obtain a solution;
    adding approximately an equimolar amount of sodium hydroxide in water to the solution;
    filtering the solution to obtain a phentolamine free base precipitate;
    washing and desiccating the phentolamine free base precipitate;
    dissolving equimolar amounts of phentolamine free base and alprostadil in a solvent;
    removing the solvent;
    adding diethyl ether and chilling in a dry ice acetone bath; and,
    evaporating and washing the precipitate.

4. The method of claim 3 wherein phentolamine is in the form of phentolamine mesylate.

5. The method of claim 3 wherein phentolamine is in the form of phentolamine hydrochloride.

6. The method of claim 3 wherein the solvent is ethanol.

7. The method of claim 3 wherein the quantity of phentolamine dissolved in water is at a concentration of from about 3 to about 15 mg/ml.

8. The method of claim 3 wherein the sodium hydroxide is 1 M sodium hydroxide.

9. The method of claim 3 wherein the diethyl ether is anhydrous diethyl ether.

10. The method of claim 3 wherein the precipitate is washed with diethyl ether.

11. A method of producing phentolamine alprostadilate comprising the steps of:
    dissolving a quantity of phentolamine mesylate in water to obtain a solution;
    adding approximately an equimolar amount of sodium hydroxide in water to the solution;
    filtering the solution to obtain a phentolamine free base precipitate;
    washing and desiccating the phentolamine free base precipitate; and,
    dissolving equimolar amounts of phentolamine free base and alprostadil in solvent.

12. The method of claim 11 wherein the solvent is polyethylene glycol.

13. A method of producing papaverine alprostadilate comprising the steps of:
    dissolving approximately equimolar amounts of papaverine free base and alprostadil in solvent and removing the solvent and crystallizing the resulting precipitate in a dry ice acetone bath.

14. The method of claim 13 wherein the solvent is ethanol.

15. The method of claim 13 wherein the solvent is removed under a nitrogen stream.

16. The method of claim 13 wherein the resulting precipitate is crystallized by exposure to diethyl ether.

17. The method of claim 13 wherein the solvent is polyethylene glycol and the solvent is not removed.

18. The method of claim 17 wherein the polyethylene glycol is warmed to 55° C.

19. The method of claim 13 wherein crystallization is facilitated by addition of papaverine alprostadilate crystals.

* * * * *